United States Patent [19]

Deeds et al.

[11] Patent Number: 5,210,482

[45] Date of Patent: May 11, 1993

[54] DEVICE FOR MEASURING THE ELECTRODE POTENTIAL OF UNDERWATER CONCRETE REINFORCEMENT

[75] Inventors: Patrick Deeds, Avon; Gilbert Grimaldi, Le Chatelet en Brie; André Raharinavo, Paris, all of France

[73] Assignee: L'Etat Francais représenté par le Laboratoire Central des Ponts, et Chaussees, France

[21] Appl. No.: 691,137

[22] Filed: Apr. 25, 1991

[30] Foreign Application Priority Data

Apr. 26, 1990 [FR] France .................. 90 05340

[51] Int. Cl.⁵ .................................... G01N 27/00
[52] U.S. Cl. ............................ 324/71.1; 204/404; 324/700
[58] Field of Search ........... 324/71.1, 71.2, 700, 324/715, 425; 204/404, 153.11

[56] References Cited

U.S. PATENT DOCUMENTS

| | | | |
|---|---|---|---|
| 4,611,175 | 9/1986 | Kumar et al. | 324/425 |
| 4,927,503 | 5/1990 | Polly | 204/404 |
| 4,942,354 | 7/1990 | Miller | 204/404 |
| 4,958,130 | 9/1990 | Mochizuki et al. | 324/700 |
| 5,069,774 | 12/1991 | Hladky et al. | 204/404 |

Primary Examiner—Kenneth A. Wieder
Assistant Examiner—Maura K. Regan
Attorney, Agent, or Firm—Ostrolenk, Faber, Gerb & Soffen

[57] ABSTRACT

The invention relates to a device for measuring the electrode potential of the reinforcement in underwater concrete. The device is of the type comprising a reference electrode placed against the facing of the concrete and a voltmeter connected to the reference electrode and to the reinforcement. The reference electrode is disposed in a bell suitable for pressing in watertight manner against a facing of the concrete, thereby delimiting an enclosure. The device further includes means for injecting compressed air into the enclosure and means for enabling the water imprisoned therein to escape.

10 Claims, 1 Drawing Sheet

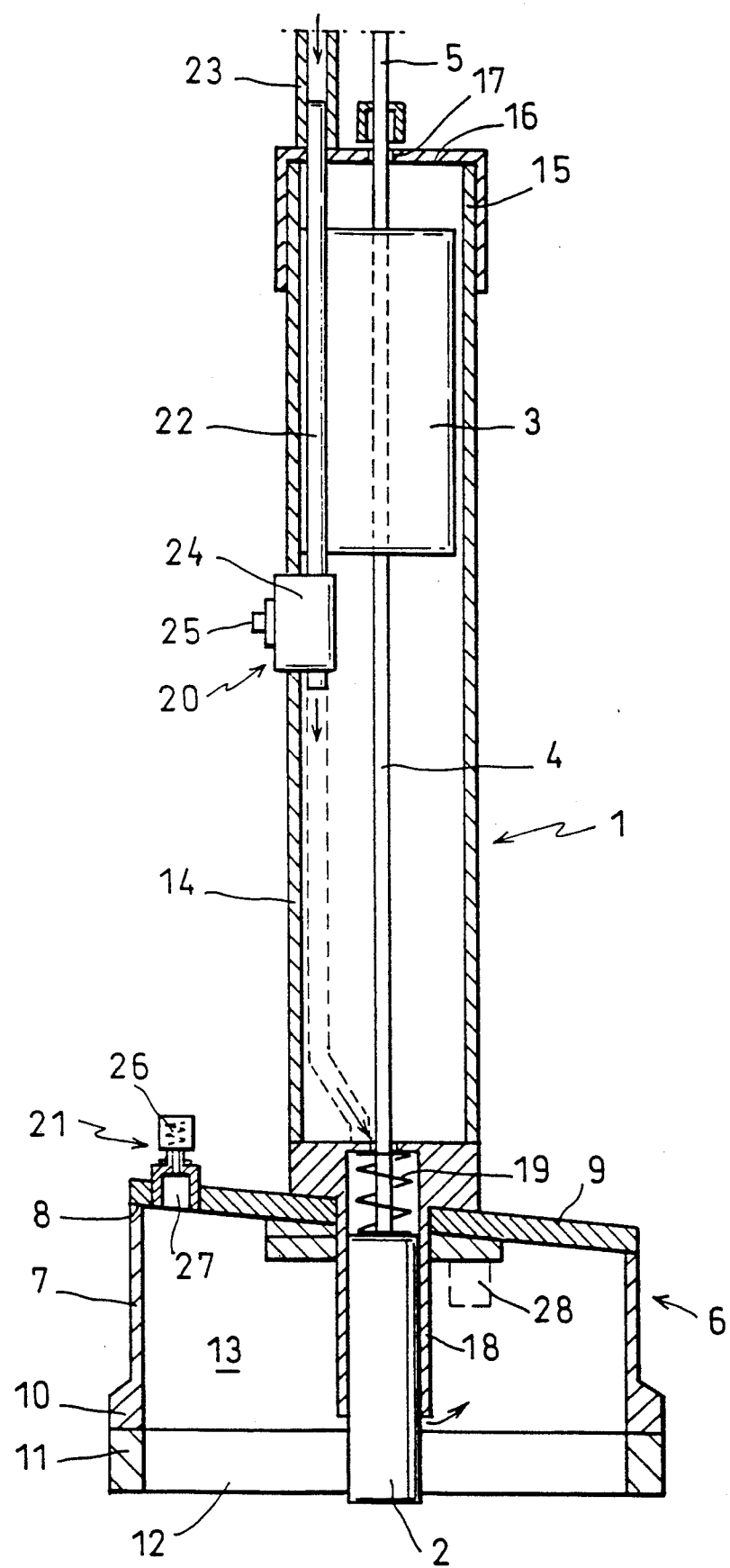

DEVICE FOR MEASURING THE ELECTRODE POTENTIAL OF UNDERWATER CONCRETE REINFORCEMENT

The present invention relates to a device for measuring the electrode potential of the reinforcement in an underwater concrete structure, the device being of the type comprising:

a reference electrode for placing against the concrete facing of said structure while the measurement is being performed; and a voltmeter connected firstly to said reference electrode and secondly to the reinforcement of said concrete structure.

BACKGROUND OF THE INVENTION

In general, reinforced concrete is an excellent material, making it possible to obtain structures having a lifetime of forty years and more provided the integrity of the material is conserved. To achieve this, it is necessary to ensure that the specifications concerning the type of cement, its proportions, the compactness of the concrete, the quality of the aggregate, and the thickness of the covering overlying the reinforcement are all satisfied.

However, corrosion may develop under conditions that are particularly aggressive for the material, such as sea water, where the presence of defects facilitates degradation of the concrete and of its reinforcement. It is therefore necessary to be able to monitor the corrosion state of the reinforcement using a methodology appropriate to obtaining as accurate a diagnosis as possible.

When a concrete structure stands in air, the commonly used method of detecting corrosion consists in measuring so-called "electrode potential". The principle consists in measuring the potential difference between the reinforcement latticework of the concrete and a reference electrode placed on the facing of the concrete. In order to locate zones of active corrosion, it is necessary to take a large number of measurements at points in a net of greater or lesser mesh size. The method is flexible in use: the apparatus is simple and suitable for connection to a data acquisition system, and in most cases measurements can be performed quickly. The main problems encountered are related to the dryness of the concrete. Too low a water content in the concrete makes the values unstable.

For moderately dry concrete in air, the measured electrode potential corresponds to a point immediately under the reference electrode. When the concrete is underwater, the measured electrode potential corresponds to a region of reinforcement adjacent to the electrode, and in addition, the presence of water around the electrode and having a greater or lesser air content disturbs the measurements and makes them unreliable.

An object of the present invention is to provide a device of the type specified above and capable of obtaining reliable measurements even when the electrode is disposed close to the reinforcement of underwater concrete.

SUMMARY OF THE INVENTION

The object of the invention is achieved by the fact that the device further includes:

a bell surrounding said reference electrode, with the mouth of the bell being delimited by a rim constituted by a deformable material, said bell being suitable for placing against the facing of the concrete structure at least while the measurement is being performed in such a manner that its mouth is closed in watertight manner by said facing, said bell, while disposed in this manner against said facing, co-operating with the facing to define a watertight enclosure in which said reference electrode is disposed to bear against said facing;

gas injection means for injecting a gas, in particular compressed air, into said enclosure so as to expel water therefrom;

water escape means to enable the water contained in said enclosure to escape therefrom under the action of said gas; and thrust means for pressing said reference electrode situated inside said enclosure against said facing.

By virtue of this structure, the water which may be imprisoned inside the enclosure when the bell is placed against the concrete facing can be expelled from said enclosure by the compressed air prior to performing the measurement. This then provides ideal conditions for obtaining reliable measurements. Naturally the shape and the weight of the device are suitable for enabling it to be manipulated by hand and in all directions.

Advantageously, the rim delimiting the bell mouth is constituted by a flexible sealing lip. It may thus fit itself against the concrete wall in spite of possible roughness of the wall and in spite of its geometrical shape.

Advantageously, the air injection means include a tube opening out into said enclosure and a cock mounted on said tube and suitable for operating by hand. The tube is permanently connected to a source of air under pressure.

Advantageously, the water escape means comprise an opening provided through the wall of said bell and a non-return valve mounted in said opening.

For the purpose of applying the reference electrode against the concrete facing of the structure, the reference electrode is mounted at the free end of a resilient telescopic system itself fixed to the bell, the telescopic system being disposed in such a manner that said electrode is movable in a direction substantially perpendicular to the axis of the bell, i.e. perpendicularly to the concrete facing.

In order to facilitate handling of the device, the bell is advantageously disposed at the end of a handle situated on the opposite side of said bell to its mouth.

The handle is preferably hollow and contains the electric cable for the reference electrode and the means for injecting compressed air. The member for operating the cock is preferably disposed on the outside wall of the handle.

In order to make it possible to be sure that the reference electrode is properly pressed against the concrete wall closing the bell mouth and that the enclosure is emptied of its water, at least a portion of the wall of the bell is transparent. In addition, it is advantageous to associate an indicator lamp with the electrode and the telescopic system, said indicator lamp being designed to light up when the reference electrode is in contact with the concrete of the structure.

BRIEF DESCRIPTION OF THE DRAWINGS

Other advantages and features of the invention appear from reading the following description of a preferred embodiment of the invention given by way of example and made with reference to the accompanying drawing, in which the sole FIGURE is a section through a device of the invention.

MORE DETAILED DESCRIPTION

The device 1 for measuring the electrode potential of the reinforcement in a concrete structure comprises, in conventional manner, a reference electrode 2 for pressing against a concrete facing of said structure, and a voltmeter 3 connected firstly to the reference electrode 2 via an electric cable 4 and secondly to the metal reinforcement of the concrete structure via a second electric cable 5.

In order to be able to use the above measuring device to measure the electrode potential of the reinforcement of a concrete structure that is totally or partially underwater, the device 1 further includes a bell 6 surrounding the reference electrode 2. By way of example, the bell 6 may be constituted by a cylindrical sleeve 7 having one end 8 closed by a plate 9. The other end 10 of the sleeve 7 is extended by a lip 11 constituting the rim of the bell and delimiting the bell mouth 12.

The lip 11 is made of a resilient flexible waterproof material, and it is long enough to be able to constitute a seal when the bell 6 is pressed against the concrete facing with the lip 11 in contact with said facing and with the mouth 12 being completely closed by a portion of the facing. The lip 11 then adapts to the shape of the annular portion of the facing against which it bears and the enclosure 13 delimited by the bell 6 and the facing is sealed in watertight manner from the outside of the bell 6.

The bell 6 is fixed to the end of a hollow handle 14 which extends from the opposite side of the bell 6 to its mouth 12. The hollow handle is fixed to the middle of the plate 9 in watertight manner. The other end 15 of the handle 14 is closed by a cover 16 provided with a sealing through hole 17 for the electric cable 5. The voltmeter 3 may be disposed inside the handle 14 and it may be read through a window provided in the wall of the handle 14. The electric cable connecting the voltmeter 3 to the reference electrode 2 is situated largely in the handle 14 and it passes through the plate 9.

The reference electrode 2 is mounted on a telescopic system 18 including a spring 19 with one end held by the assembly constituted by the sleeve 14 and the plate 9, and having its other end bearing against the reference electrode 2 in such a manner as to enable the electrode to move substantially parallel to the axis of the bell 6, i.e. in a direction perpendicular to the plane of the bell mouth 12. At rest, the reference electrode projects a little beyond the enclosure 13, and when the bell 6 is pressed against the concrete facing, the spring 19 exerts a force on the reference electrode 2 in such a manner as to ensure that it is pressed properly against the concrete facing.

The device 1 further includes means 20 for injecting compressed gas into the enclosure 13 so as to expel water therefrom, and means 21 to enable the water imprisoned in the enclosure 13 to escape from the device under the action of the gas. The gas may advantageously be compressed air.

The means 20 for injecting compressed air into the enclosure 13 are essentially constituted by a tube 22 disposed inside the handle 14 and opening out both into the enclosure 13 and into the cover 16. The tube 22 may be connected in conventional manner to a source of air under pressure by means of a hose 23. A cock 24 is provided in the air delivery path and has a control member 25 situated outside the handle 14. The control member 25 may advantageously be a pushbutton controlled by the thumb of the operator holding the handle 14 in the hand.

The means 21 for allowing the water imprisoned inside the enclosure 13 to escape therefrom are constituted by a non-return valve 26 mounted in an opening 27 provided through the plate 9 close to its periphery.

To make it possible for the operator to check that the water has been expelled from the enclosure 13 and that the reference electrode 2 is pressed properly against the concrete facing, the plate 9 is advantageously made of a material which is rigid and transparent, and an indicator lamp 28 is connected in conventional manner to the spring 19 or to the reference electrode 2 so as to light up when the spring 19 is exerting sufficient force on the reference electrode 2.

The operation of the device 1 is easily understood. The operator, who may be a diver, holds the device by its handle 14. The bell 6 is pressed against the concrete facing. When the bell 6 is properly pressed, the indicator lamp 28 lights up. The operator then presses on the pushbutton 25, thereby injecting air into the enclosure 13. Water escapes from the enclosure 13 via the non-return valve 26. When air escapes via the non-return valve, the operator releases the pushbutton 25. The operator can then proceed to read the measurement. It should be observed that the non-return valve 26 prevents water from penetrating back into the enclosure 13 via the opening 27. The pressure inside the enclosure 13 is never greater than the pressure outside it. It may be slightly lower, in which case the bell 6 is held against the concrete wall like a suction cup. In use, the non-return valve 26 should be at the bottom of the enclosure 13.

Numerous variants may be made to the embodiment described above. In particular, the voltmeter may be connected to a system for taking and acquiring measurements. The voltmeter may also be disposed outside the device. The bell may be held against the facing by a mechanical device instead of by hand. The important point is that the faces delimited by the handle 14 and the bell 6 should be completely watertight while the device is in use. The concrete structure mentioned in the present description may constitute a fixed structure or it may constitute a movable structure such as a concrete hull.

We claim:

1. A device for measuring the electrode potential of the reinforcement in an underwater concrete structure, the device being of the type comprising:
    a reference electrode for placing against the concrete facing of said structure while the measurement is being performed; and
    a voltmeter connected firstly to said reference electrode and secondly to the reinforcement of said concrete structure;
the device further including:
    a bell surrounding said reference electrode having a mouth delimited by a rim comprising a deformable material, said rim being placed against the facing of the concrete structure at least while the measurement is being performed such that said mouth is closed in watertight manner by said facing, and such that said bell defines with said facing a watertight enclosure in which said reference electrode is disposed to bear against said facing;
    gas injection means for injecting a gas, into said enclosure so as to expel water therefrom;

water escape means to enable the water contained in said enclosure to escape therefrom under the action of said gas; and thrust means for pressing said reference electrode situated inside said enclosure against said facing.

2. A device according to claim 1 wherein the rim delimiting the bell mouth comprises a flexible sealing lip.

3. A device according to claim 1 wherein the gas injection means include a tube opening out into said enclosure and a cock mounted on said tube suitable for hand operation.

4. A device according to claim 1 wherein the water escape means comprises an opening provided through the wall of said bell and a non-return valve mounted in said opening.

5. A device according to claim 1 wherein the thrust means for applying said reference electrode against the concrete facing of the structure comprises a telescopic system provided with a spring interposed between said electrode and said bell, and disposed in such a manner that said electrode is movable in a direction substantially parallel to the axis of the bell.

6. A device according to claim 1 wherein the bell is disposed at the end of a handle situated on the opposite side of the bell to its mouth.

7. A device according to claim 1 wherein said handle is hollow and contains the electric cable for the reference electrode and the compressed gas injection means.

8. A device according to claim 1 wherein at least a portion of the bell wall is transparent.

9. A device according to claim 8 including an indicator lamp associated with the reference electrode for illuminating when the reference electrode comes into contact with the concrete facing of the structure.

10. A device according to claim 1, wherein the gas injection means comprises an injection means.

* * * * *